United States Patent [19]
Fulton

[11] Patent Number: 6,074,374
[45] Date of Patent: Jun. 13, 2000

[54] CATHETER WITH LUMEN OCCLUDING MEANS

[75] Inventor: Richard E. Fulton, Grand Junction, Colo.

[73] Assignee: Angiodynamics, Inc., Queensbury, N.Y.

[21] Appl. No.: 09/127,592

[22] Filed: Jul. 31, 1998

[51] Int. Cl.$^7$ .................................................. A61M 5/00
[52] U.S. Cl. ........................ 604/249; 604/247; 604/96; 604/264; 604/523
[58] Field of Search .............................. 604/247, 96, 264, 604/246, 249, 266, 269, 523, 537, 544, 540, 507–510, 27, 28, 31

[56] References Cited

U.S. PATENT DOCUMENTS

| | | |
|---|---|---|
| 4,475,898 | 10/1984 | Brodner et al. . |
| 4,650,466 | 3/1987 | Luther . |
| 4,801,297 | 1/1989 | Mueller . |
| 5,250,034 | 10/1993 | Appling et al. . |
| 5,348,537 | 9/1994 | Wiesner et al. . |
| 5,624,413 | 4/1997 | Markel et al. . |
| 5,647,846 | 7/1997 | Berg et al. . |
| 5,664,567 | 9/1997 | Linder . |
| 5,718,692 | 2/1998 | Schon et al. . |
| 5,776,111 | 7/1998 | Tesio . |
| 5,957,901 | 9/1999 | Mottola et al. ........................ 604/264 |

*Primary Examiner*—Corrine McDermott
*Assistant Examiner*—Cris L. Rodriguez
*Attorney, Agent, or Firm*—McAulay Nissen Goldberg Kiel & Hand, LLP

[57] ABSTRACT

A catheter for use with the vascular system includes an elongated catheter body which has a side wall defining an interior catheter lumen. A plurality of openings are provided in the side wall at a first distal zone of the catheter body. The openings are adapted for relatively low pressure movement of fluid therethrough. A plurality of normally closed pressure responsive exits are located in a side wall at a second distal zone of the catheter body, the second distal zone being spaced from and positioned proximal of the first distal zone. The pressure responsive exits permit fluid material to exit from the catheter lumen in response to internal fluid pressure which is greater than a predetermined magnitude. An intermediate zone is located between the first and second distal zones. A removable occluding member is adapted to be positioned within the catheter lumen. The occluding member has a sealing element with a collapsed insertion state and an expanded sealing state. When the sealing element is in the sealing state and positioned in the intermediate zone, it can be expanded to contact the inside surface of the side walls of the lumen in order to seal off fluid communications between the first and second distal zones. When the occluding member is in the sealed position, enzymatic fluid material is inserted through the lumen at a pressure greater than the predetermined magnitude to cause it to pass through the pressure responsive exits in order to contact any fibrin built up along the outside surface of the elongated catheter body radially expanding the catheter body causing the fibrin to loosen, dissolve and dissipate.

35 Claims, 6 Drawing Sheets

CATHETER WITH LUMEN OCCLUDING MEANS

FIELD OF THE INVENTION

The present invention relates generally to the field of catheters for long term use in delivering and removing fluid material into or from the vascular system, and more particularly, to such a catheter having a means for occluding a portion of the catheter to enable pressure responsive orifices to open in the catheter body in order to facilitate removal of fibrin build up on the outside surface of the catheter when the catheter is inside the vasculature.

BACKGROUND OF THE INVENTION

Elongated catheters for obtaining access to a vascular system are well known in the art and have been used in the medical field for many years. Such catheters usually have an elongated body with proximal and distal ends. A catheter lumen is formed interiorly of the body. A hole or opening is located at the distal end of the elongated body so that fluid material can either pass from the catheter lumen through the hole into the vascular system or so that fluid from the vascular system may be drawn through the distal end hole into the catheter lumen to be withdrawn from the vascular system. Fluid material which is intended to be infused into the vascular system is introduced into the catheter lumen through its proximal end. Pressure responsive exits in the form of slits may be arranged in the side wall of the catheter body as a means for infusing fluid which is under a desired pressure from the catheter lumen into the vascular system at a desired rate and at a desired location.

Catheters of the foregoing type have been used for a variety of purposes. While some applications do not require that the catheter remain in the vascular system for any significant length of time, other uses or medical procedures, such as dialysis, may require that the catheter remain in the vascular system for long periods of time. While the typical catheter in use today is made of polymeric material, which is biocompatible, such materials are not of natural origin. As a result, the longer a catheter remains in the vascular system, the more likely it is that deposits of fibrin will form on the outside surface of the catheter body. Over time, such deposits will build up, forming a fibrin sheath along the outside surface of the catheter. The formation of fibrin build up and the creation of such a fibrin sheath on the outside surface of a catheter within a vascular system can have serious deleterious effects. Fibrin forms an attractive environment for the growth of bacteria. Although small amounts of bacteria in a human body may not cause serious problems as the natural defenses of the human body can combat the effects of such small amounts of bacteria, the presence of a fibrin build up or sheath provides an environment where bacteria can accumulate and grow. The growth of bacteria at such a site may therefore result in infections. The occurrence of such an infection will require a course of anti-biotic treatment and usually the removal of the catheter in order to overcome the bacterial infection and to allow the patient to recover from its effects. Not only will the patient now have to overcome the effects of an infection, but the patient is not receiving the benefit of the treatment which required the use of the catheter in the first place.

The build-up of a fibrin sheath on the outside wall of a catheter in a vascular system may also cause the partial or complete obstruction of holes and openings, such as at the distal end of the catheter, thereby ihibiting or preventing the passage of fluid material through the holes either into the vascular system or from the vascular system. Thus, when attempting to infuse or withdraw fluids into or from the vascular system, or during such procedures as dialysis, the catheter will not be able to handle the required flow rates.

Heretofore, the solution to the build up of a fibrin sheath has been to replace the catheter with a new one, requiring significant cost and time, or to physically remove the fibrin from the outside walls of the catheter body while the catheter remains in place within the patient's vascular system. The procedure to accomplish this removal of the fibrin sheath involves an additional entry into the patient's vascular system so that a mechanical device, such as an expanding basket or snare, may be inserted into the vascular system and manipulated to the site of the catheter. The basket or snare is then used to strip the fibrin build up from the outside surface of the catheter, thus freeing up the openings to allow fluid to pass through the catheter into or from the vascular system and to eliminate an environment that would promote the growth of bacteria. Such a procedure for stripping the fibrin material from the outside surface of the catheter, however, results in the sudden release and availability of large amounts of fibrotic material which may travel through the patient's vascular system to the lungs with disastrous results. In addition, the use of such mechanical devices as a basket or snare, will cause damage to the catheter which could result in its subsequent failure. Such a stripping procedure is also expensive.

OBJECTS OF THE INVENTION

It is accordingly a principal object of the present invention to provide a catheter with the means to facilitate removal of fibrin build up on the outside walls of a catheter during extended use in a manner which overcomes the foregoing disadvantages.

A more specific object of the invention is to provide a catheter having an elongated catheter body with side walls forming an interior lumen. A plurality of openings are formed in the side wall in a first distal zone of the catheter body through which fluid at relatively low pressure may pass into or from the vascular system. The catheter body is also provided with a plurality of normally closed pressure responsive exit slits in the side wall at a second distal zone located proximal of the first distal zone. Means are provided for sealing the lumen between the exit slits and openings so that fibrin treating material, such as an enzyme which can solubilize the fibrin, may be supplied through the lumen under elevated pressure and thus be caused to exit the pressure responsive slits to chemically and mechanically remove the fibrin build up along the catheter body.

Another object of the invention is to provide a catheter which will expand when fluid under relatively high pressure is inserted into it, thus causing fibrin build-up to break up, and which has pressure responsive exit slits through which therapeutic fluid under high pressure will exit thus also breaking up a fibrin sheath on the outside surface of the catheter body.

Another object of the present invention is to provide a catheter having an elongated body formed by side walls and a lumen interiorly of the side walls with openings at one distal zone to allow passage of fluid material therethrough at a relatively low pressure, and a second distal zone having exit slits through which fluid may pass under relatively high pressure, and a means for sealing the interior lumen at a location between the first and second distal zones to allow passage of therapeutic or fibrinolytic material which will come into contact with in order to dissolve and cause removal of the fibrin buildup.

Yet a further object of the invention is to provide a method for removing fibrin build up from the outside surface of a catheter within a vascular system, while overcoming the disadvantages of prior techniques, by injecting into the catheter an enzymatic material capable of solubilizing the fibrin so that it can come in contact with the fibrin in order to dissolve it.

BRIEF DESCRIPTION

The invention is directed to a catheter for use with the vascular system which has an elongated catheter body formed by a side wall defining an interior catheter lumen. A plurality of openings are provided in the side wall in a first distal zone. These openings are adapted for passage of fluid material therethrough at relatively low pressures. A plurality of normally closed pressure responsive exit slits are also formed in the side wall at a second distal zone, which is spaced from and proximal of the first distal zone. Fluid material can pass through the pressure responsive exit slits as a result of fluid pressure greater than a predetermined level. A removable sealing member having a sealing portion with a collapsed insertion state and an expanded sealing state is provided for insertion into the lumen. The sealing portion of the removable sealing member is positioned to occlude a portion of the lumen to prevent passage of fluid material through the openings so that fibrin treating material is caused to pass through the exit slits and come in contact with any fibrin build up on the outside surface of the catheter in order to solubilize the fibrin, thus causing removal of the fibrin material.

The foregoing and other features of the present invention are more fully described with reference to the following drawings annexed hereto.

DESCRIPTION OF THE PREFERRED EMBODIMENTS

Figure 1:
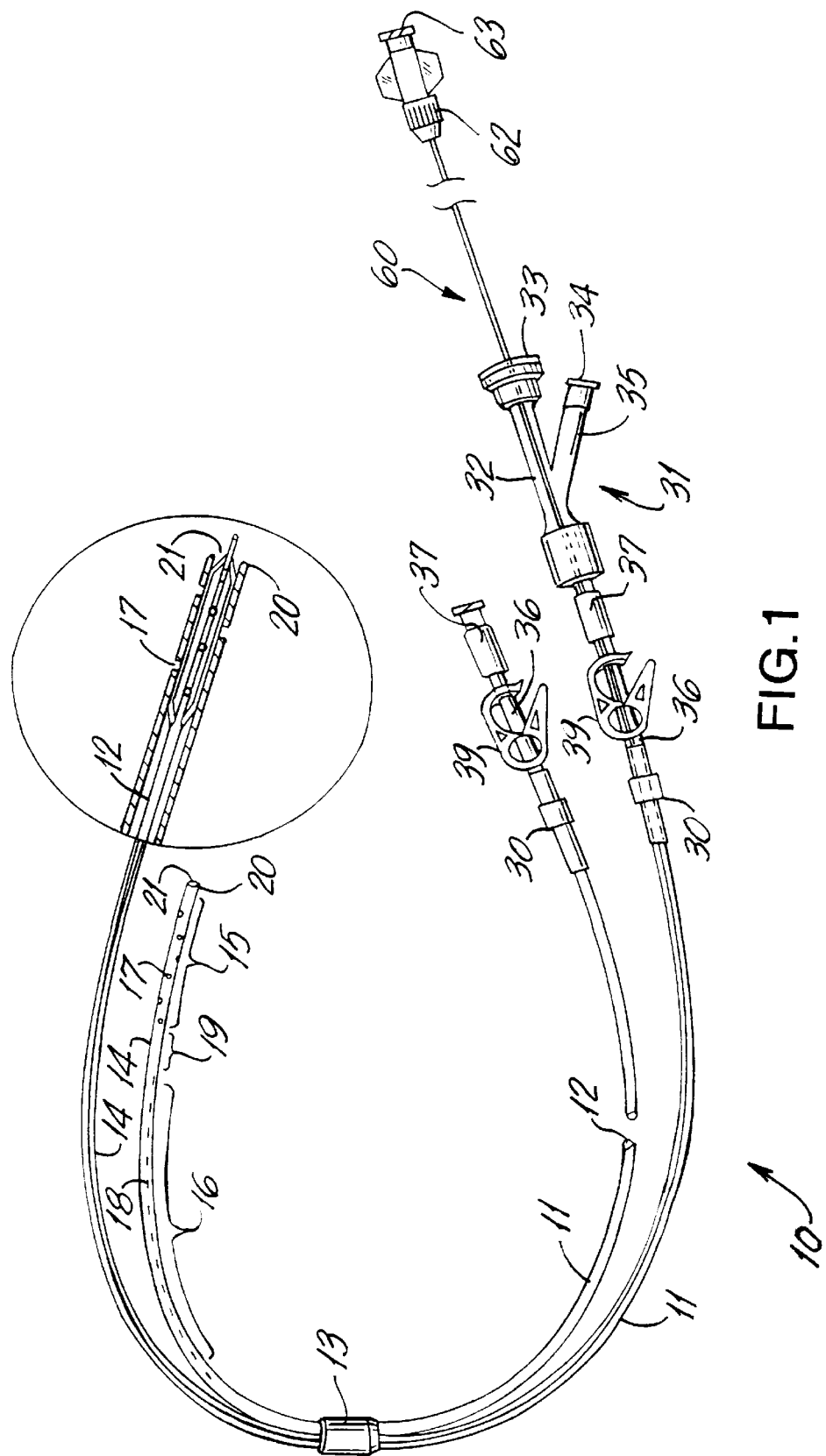
FIG. 1 is a perspective view with an enlarged area shown in section, illustrating two catheters according to the present invention, which are arranged for a medical procedure, such as dialysis.

Referring now to the drawings, and with particular reference to FIG. 1, reference numeral 10 denotes an in-dwelling catheter assembly formed by two identical catheter bodies 11 which may be used together for an application such as dialysis. The cross sectional shape of catheter bodies 11 may be circular or D-shaped in order to fit together. In such use, one of the catheter bodies will be used for withdrawing vascular fluid or blood and the other catheter body may be used for infusing treated blood or other fluid material into the vascular system The two catheter bodies are supported together by a coupling sleeve 13. Each catheter body 11 has a side wall 14 forming an interior lumen 12 which extends longitudinally through the catheter body terminating at distal end 20. A hole 21 is located at the distal end of the catheter body for use in passing fluid into the vascular system. Each catheter body 11 has a first distal zone 15 and a second distal zone 16. Distal zone 16 is spaced from and located proximal to the first distal zone 15. The space between the first and second distal zones 15 and 16 respectively defines a third distal zone 19. Within the first distal zone 15 there are a plurality of openings or holes 17 which extend through the side wall 14 of each catheter body. In a preferred design, six such holes, having a diameter of between 0.025 inches and 0.075 inches and preferably 0.052 inches, are provided. Holes 17 provide means for additional fluid communication between the vascular system and the lumen 12. Fluid material under relatively low pressure can easily pass through the holes 17. Vascular fluid material may therefore enter the holes 17 into the lumen of one of the catheters for withdrawal. Fluid material to be infused into the vascular system will be injected into lumen 12 at the proximal end of the catheter body 11 and will pass through the lumen of one of the catheters so that it may be introduced into the vascular system through holes 17. Because the catheter bodies 11 are intended to be moved through a vascular pathway which may not be straight, the bodies are usually made of a polymeric material for flexibility, expandability and chemically compatible for use with a variety of fluid materials.

The second distal zone 16 is spaced from the first distal zone by a distance of between about 0.15 inches and 0.25 inches. In a preferred design such distance will be 0.197 inches. Distal zone 16 has a plurality of pressure responsive exit slits 18 which permit fluid material to exit the catheter lumen in response to internal fluid pressure which exceeds a predetermined level. Pressure responsive exit slits 18 thereby serve as pressure valves for infusion purposes as described more fully in U.S. Pat. No. 5,250,034. A compression fitting 30 is assembled with and located at the proximal end of each catheter body 11. A tubular extension 36 is removably carried by fitting 30. A luer adaptor 37 is supported at the proximal end of extension 36 and is adapted to receive means for either introducing fluid into the lumen 12 or for withdrawing fluid therefrom, such as the hemostasis Y-adapter 31. Y-adapter 31 has a side portion 35 terminating with side port 34, and a straight portion 32 with proximal port 33. Side portion 35 and straight portion 32 each have a lumen for fluid communication with lumen 12 of catheter body 11. Fluid material to be infused into or withdrawn from the vascular system through catheter body 11 will be introduced or withdrawn via side port 34. Clamps 39 are carried by the extension 36 in order to close fluid flow therethrough.

A removable occluding or sealing member 60, described in greater detail below, is inserted into lumen 12 of the catheter body 11 through straight portion 32 of the Y-adapter 31.

Figure 2:
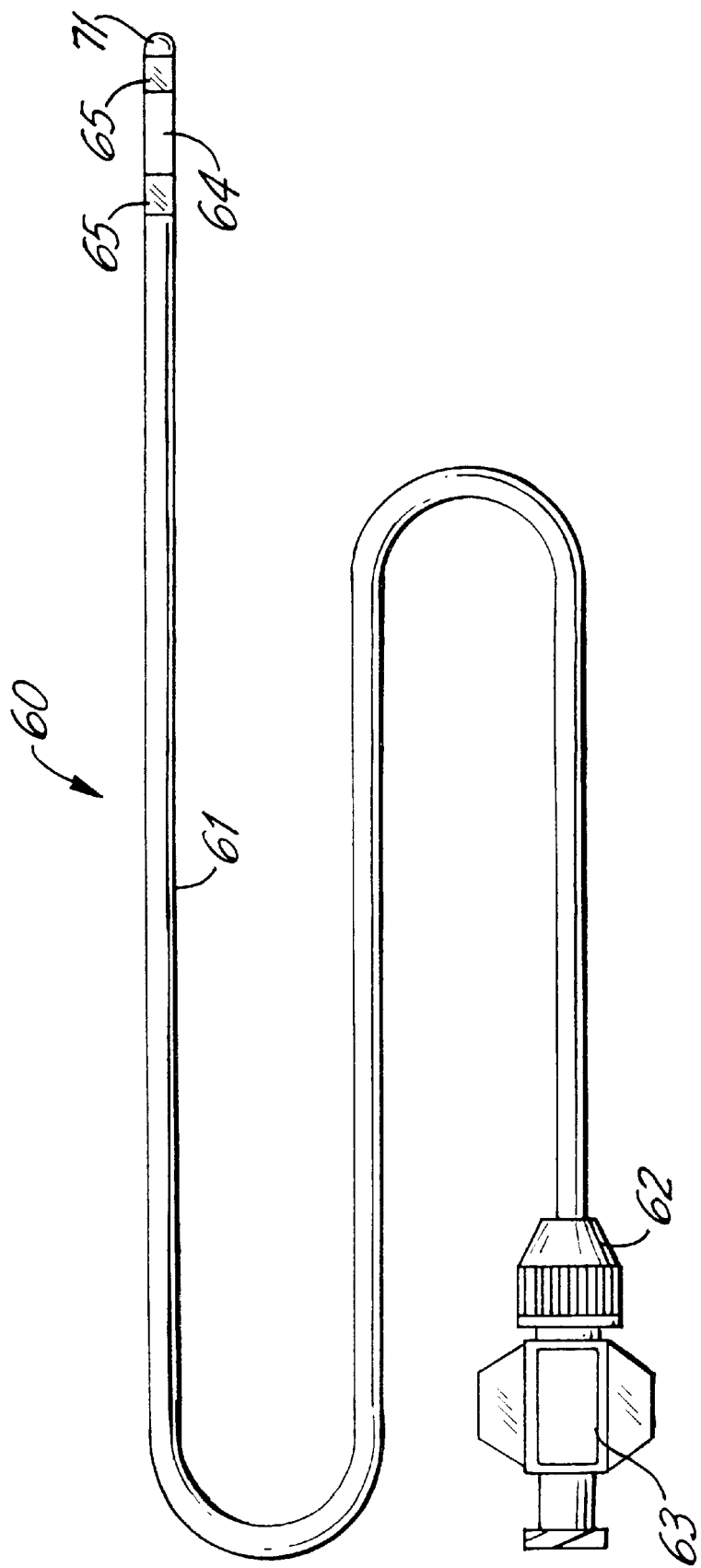
FIG. 2 is a plan view of one embodiment of a removable sealing member according to the present invention.
Figure 3:
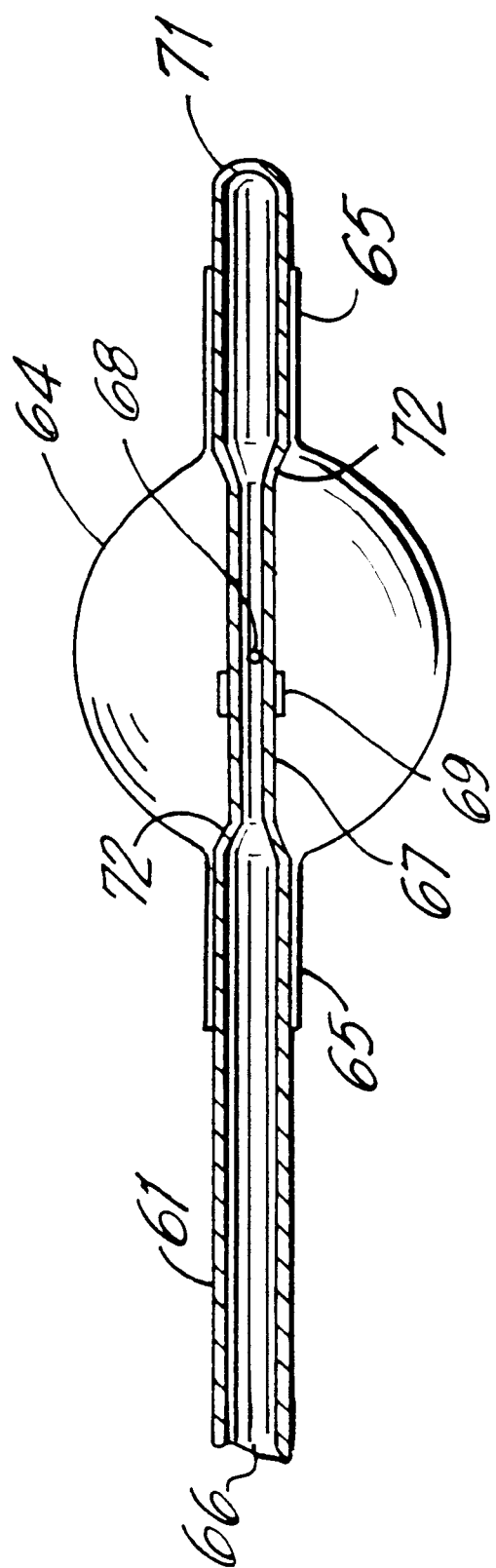
FIG. 3 is a partial sectional view of a catheter body with the removable sealing member illustrated in the embodiment of FIG. 2 shown in its expanded state.
Figure 4:
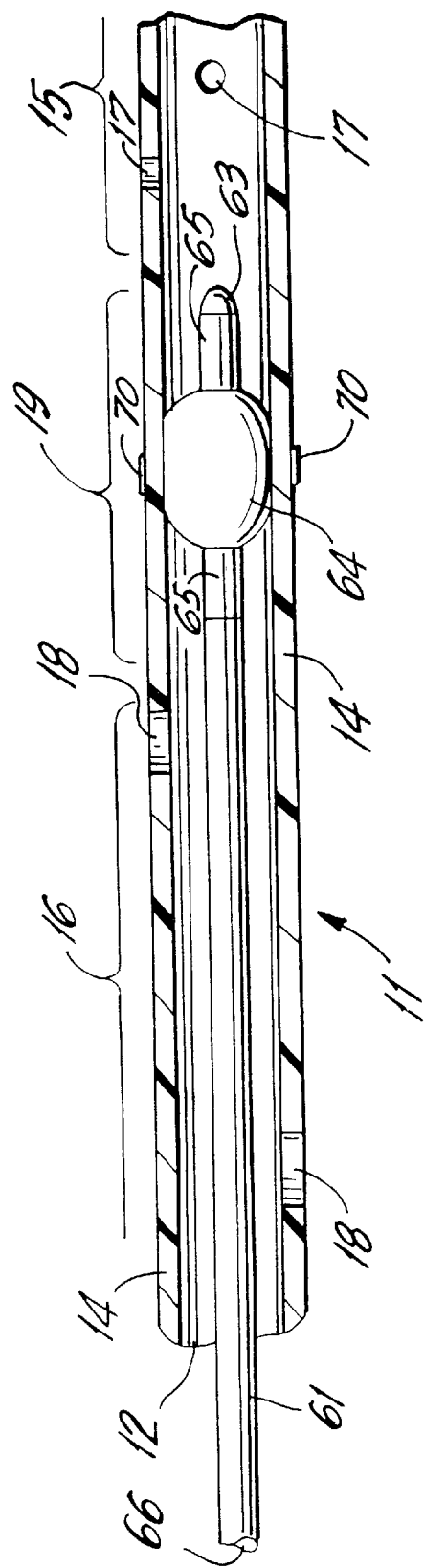
FIG. 4 is an enlarged partial sectional view of a portion of the sealing member illustrated in FIGS. 2 and 3 shown in a position inserted in the catheter body and in its expanded state.

With reference now to FIGS. 2, 3, and 4, one embodiment of the removable occluding member 60 is illustrated. Occluding member 60 has a flexible polymeric hollow shaft 61 having lumen 66 formed by its hollow interior. Located at the proximal end of shaft 61 is a hub 62 and a female luer adapter 63 connected with the hub 62. A sealing element in the form of an expandable balloon 64, also made of flexible polymeric material, with thickness between 0.0005 inches and 0.020inches, but preferably about 0.010 inches, is carried at the distal end of shaft 61. Shaft 61 is arranged to extend through balloon 64. Balloon 64 is secured to shaft 61 at the points where shaft 61 passes through it such as by adhesive or heat bonding bands 65. Distal end 71 of shaft 61 is closed and rounded for easy insertion through Y-adapter 31 into lumen 12. FIG. 2 illustrates balloon 64 in its deflated or collapsed condition. FIGS. 3 and 4 illustrate balloon 64 in its inflated or expanded condition. As will be appreciated from FIG. 3, the outside diameter of shaft 61 transitions and necks down at shoulders 72 in the area where balloon 64 is connected to the shaft 61 to form a reduced diameter shaft segment 67. The outside diameter of shaft 61 on both the distal and proximal sides of balloon 64 is preferably a number 4 French, while the outside diameter of shaft segment 67 which extends through the balloon, will be a number 3 French. In this manner, when the balloon is collapsed, the outside diameter of the area between shoulders 72 with the balloon covering the reduced diameter shaft segment 67 will be substantially the same as the outside diameter of shaft 61 on either side of the connector bands 65. Shaft 61 with the balloon in its deflated condition can thereby easily be inserted into the catheter body 11 and maneuvered to a desired location without the balloon protruding and interfering with such insertion or engaging the inside walls of the catheter body, and thus possibly being damaged.

When the occluding member 60 has been inserted into lumen 12 and it is desired to inflate balloon 64 in order to occlude or seal a portion of the lumen, a fluid material, such as saline, may be injected through female luer adapter 63 into lumen 66 within shaft 61. Exit hole 68 is located in the shaft segment 67 of shaft 61. Saline which is introduced into the shaft lumen 66 will exit hole 68 into the balloon 64 causing it to expand. When occluding member 60 is inserted into catheter body 11 and balloon 64 is inflated as a result of the injection of saline through shaft 61, balloon 64 will, when adequately expanded, engage the inside surface of side walls 14 of catheter body 11, thus occluding lumen 12. In order to accurately position balloon 64 at a desired location within lumen 12 of catheter body 11, a radio-opaque marker 69, such as a band of platinum iridium, may be applied to the outside diameter of the shaft segment 67. Under fluoroscopic observation, the marker 69 can be observed as it is being inserted into the catheter body 11. A similar marker 70 is carried on the outside surface of catheter body 11 at a point which will designate zone 19 between the first distal zone 15 and the second distal zone 16. By lining up markers 69 and 70, balloon 64 can be positioned in the zone 19 so that when it is inflated and the balloon engages the inside of walls 14, it will block or occlude fluid communication between distal zones 15 and 16. In order to remove any fibrin build up on the outside surface of catheter body 11, enzymatic material, such as urokinase, is introduced through side port 34 of Y-adapter 31, so that it will travel through lumen 12 under elevated pressure. Distal flow of the enzymatic material will be blocked by balloon 64. The enzymatic fluid will cause the body of the catheter to radially expand and will be caused to pass from lumen 12 through exit slits 18 to the outside surface of catheter body 11 where it will come in contact with any fibrin build up. As a result of the contact of the enzymatic material with the fibrin on the outside surface of catheter 11 and as a result of the mechanical effect of the radially expanding catheter body 11 caused by the pressurized fluid in lumen 12, fibrin will break up, solubilize and be carried away with the blood flow in the vascular system surrounding the catheter. As a result of such removal of the fibrin on the catheter surface, an environment for bacterial growth will be dissipated and the holes 17 and slits 18 will be unclogged by any build up of fibrin in these areas.

Figure 5:
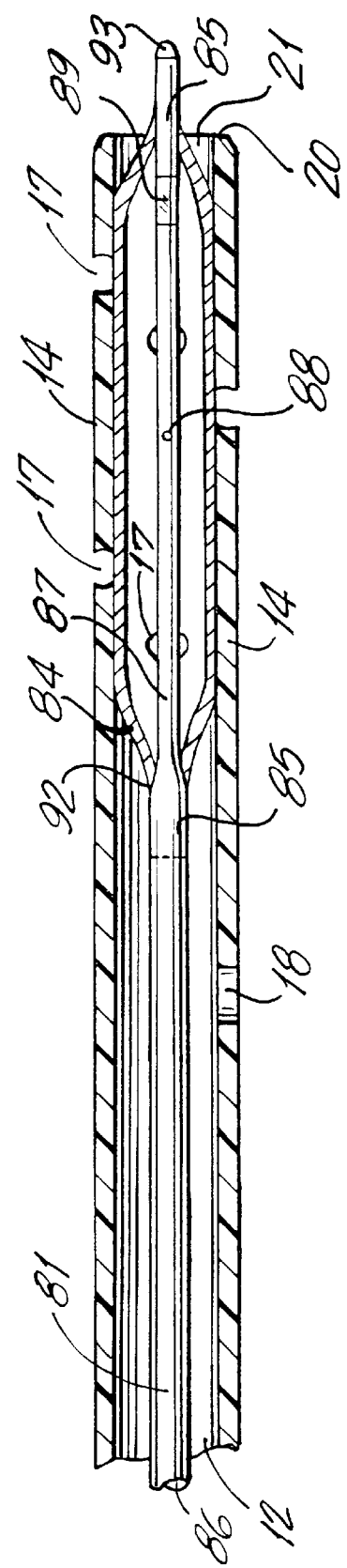
FIG. 5 is a view similar to that of FIG. 4 illustrating a removable sealing member within a catheter body according to a further embodiment of the present invention.

Turning now to FIG. 5, an alternate embodiment of an occluding member is illustrated. In this embodiment, reduced diameter shaft segment 87 of shaft 81 will extend from transition shoulder 92 to the distal end 93. Balloon 84, which may be a non-compliant balloon made of expandable polymeric material having a preferred thickness in this embodiment of about 0.001 inches, serving as the sealing element will be secured to shaft 81 by adhesive or thermal bonding welded bands 85 so that balloon 84 extends over a longitudinal distance larger than the longitudinal distance of zone 15. Radio opaque marker 89 can be observed under fluoroscopy during insertion in order to locate marker 89 at approximately the distal end 20 of catheter body 11 without the need for a marker on body 11 to line it up with. Distal end 93 of reduced diameter segment 87 will protrude through end hole 21 of body 11. When saline is injected through lumen 86 of shaft 81 it will exit hole 88 to fill up balloon 84 causing it to expand. When so expanded, balloon 84 will engage the inside surface of wall 14. In the case of the embodiment shown in FIG. 5, because the balloon 84 extends at least the entire length of zone 15, the inflated balloon will cover all of the holes 17 within the zone 15. Enzymatic fluid introduced into lumen 12 will again be caused to exit slits 18 in order to contact any fibrin material which may have built up on the outside surface of catheter body 11 in order to dissolve it.

Figure 6:
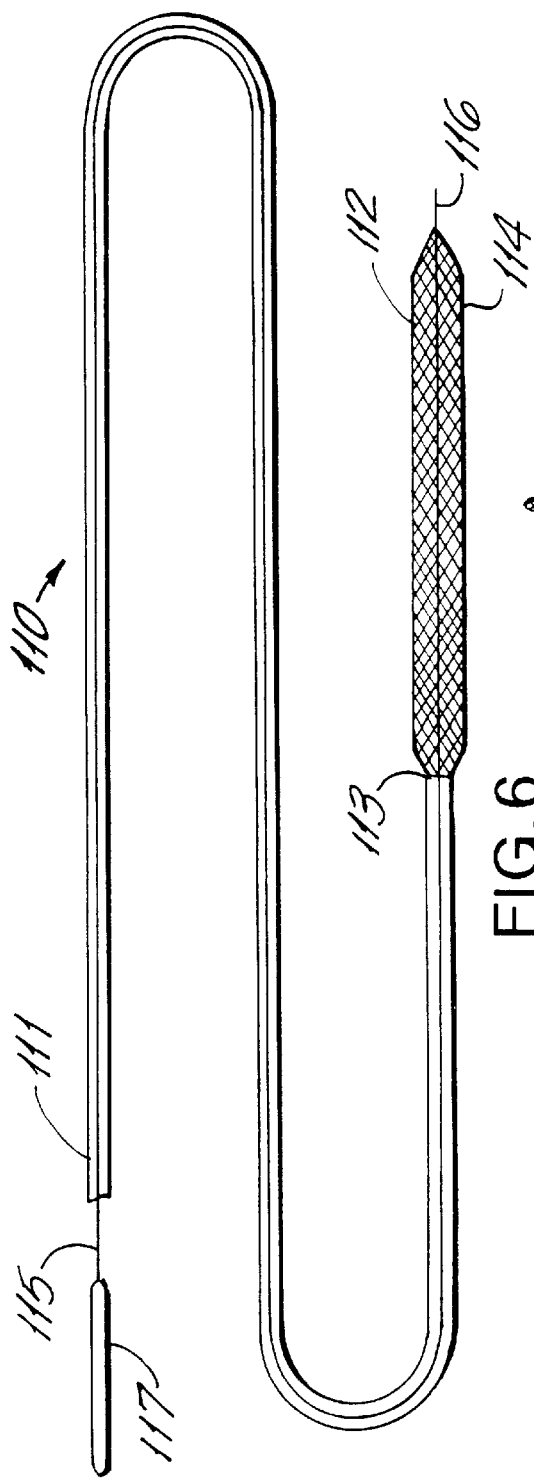
FIG. 6 is a plan view of a removable sealing member according to another embodiment of the present invention shown in its collapsed state.
Figure 7:
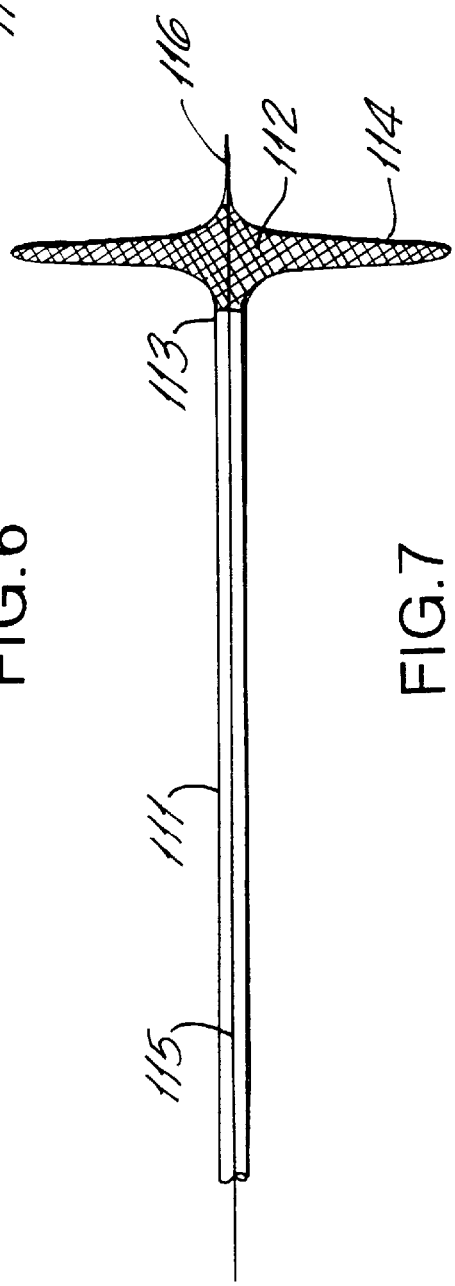
FIG. 7 is a plan view of the removable sealing member illustrated in FIG. 6 shown in its expanded state.

A further embodiment of an expandable occluding or sealing member is illustrated in FIGS. 6 and 7. In this embodiment, occluding member 110 includes a flexible hollow polymeric shaft 111. The sealing element of this embodiment is a flexible covered mesh basket 112, which can be made either of metal or plastic. The basket 112 is attached to the distal end 113 of the shaft 111. Basket 112 has a polymeric flexible covering 114. An adjusting wire 115 extends through the hollow center of the shaft 111 and is connected to the distal end 116 of basket 112. A handle 117 for gripping is located at the proximal end of wire 115. FIG. 6 illustrates wire mesh basket 112 in its collapsed state. Longitudinal movement of wire 115 in the proximal direction will cause distal end 116 to move toward connection point 113 causing basket 112 to expand in a radial direction as illustrated in FIG. 7. In this manner, outer covering 114 of the wire mesh basket 112 is caused to engage the inside surface of walls 14 of catheter body 11 when the occluding member 110 is inserted into the lumen 12. A radio opaque marker may also be carried by the occluding device 110, in a manner similar to that described with respect to the embodiments of FIGS. 2 and 5, in order to be able to locate the expandable covered wire mesh basket at a desired location within the catheter body 11. Moving wire 115 in a distal direction will cause distal end 116 to move in a distal direction away from connection point 113 causing the covered wire mesh basket 112 to collapse into its collapsed state so that the occluding device 110 may be removed or repositioned within the lumen 12 of catheter body 11.

In operation, an occluding member such as member 60 of the embodiments illustrated in FIGS. 1 or 2, or the occluding member 110 of the embodiment illustrated in FIGS. 6 and 7, is inserted through port 33 of the straight portion 32 of the Y-adapter 31 when it is desired to remove any build up of fibrin on the outside surface of the catheter body 11. In a catheter design which has zone 15, with holes 17, and zone 16, with slits 18, the sealing element of the occluding member is placed proximal of the first hole 17, within the area of zone 19 by fluoroscopically observing the radio opaque markers. The sealing element of the occluding member will then be expanded to engage the inside surface of walls 14 thus blocking any fluid flow distally of the sealing element. Enzymatic fluid is then injected via side port 34 into the lumen 12 of catheter body 11 under appropriate pressure so that it will exit lumen 12 through exit slits 18 in order to come into contact with fibrin build up causing the fibrin to dissolve and dissipate. The introduction of the enzymatic fluid under appropriate pressure into lumen 12 will also cause catheter body 11 to radially expand enough to mechanically disrupt and cause a break up of the fibrin sheath on the outside surface of the catheter body. In addition, the mechanical effect of fluid exiting slits 18 will also result in breaking up the fibrin sheath. Accordingly, even if enzymatic fluid were not used but another therapeutic fluid or non-reactive fluid (such as saline) were used instead, the foregoing mechanical actions would be effective in facilitating removal of the fibrin.

In the case of the embodiment shown in FIG. 2, when properly located, the balloon 64 can be inflated by the introduction of saline through lumen 66 of shaft 61 until the balloon is fully inflated engaging the inside surface of side walls 14 thus blocking passage of any enzymatic fluid distally beyond the location of the balloon. After the enzymatic material or other therapeutic fluid has been injected and exited through the slits 18, saline can be removed from the balloon by drawing it back out through the shaft 61. The occluding member 60 can then either be removed from the catheter body 11 by withdrawing it out of the Y-adapter 31, or its sealing element may be repositioned within the catheter body. If the catheter body 11 is of a design without any side holes, the sealing element of the occluding member may be advanced to the distal end of the catheter. Once in place, the expandable sealing element of the occluding member is expanded or deployed, thus sealing off any flow in the catheter distally of the expanded sealing element.

If the holes 17 of the catheter body also need to be cleared of fibrin material, this can be accomplished by collapsing the sealing element of the occluding member and repositioning it distally of zone 15, expanding it once again and reintroducing enzymatic material so that it may pass through the holes 17, thus dissolving any fibrin material within the holes 17.

After the outside surface of the catheter and the holes 17 are cleared of fibrin by the administration of enzymatic or other therapeutic material, the occluding member is removed from the catheter body and the catheter reused in its intended fashion.

The present invention can thus be used to quickly and easily remove any fibrin build up or sheath which may be formed on the outside surface of the catheter body without having to mechanically strip the fibrin from the outside surface by using snares or baskets. Use of the present invention thus provides a means to eliminate the sudden release of fibrotic material which may travel to the patient's lungs and avoids the requirement of an additional entry site created in the body of the patient in order to insert snares or other mechanical devices needed to scrape the outside surface of the catheter body. Use of the present invention also eliminates possible damage to the catheter body, thus extending its useful life. Elimination of fibrin build up on the outside surface of the catheter body in a manner described in accordance with the present invention will reduce or eliminate possibilities of infection which would be promoted by the environment of a fibrin build up.

This invention has been described and illustrated in connection with certain preferred embodiments which are illustrative of the principles of the invention. However, it should be understood that various modifications and changes may readily occur to those skilled in the art, and it is not intended to limit the invention to the constructions and operation of the embodiments shown and described herein. Accordingly, additional modifications and equivalents may be considered as falling within the scope of the invention as defined by the claims herein below.

The embodiments of the invention in which an exclusive property or privilege is claimed are defined as follows:

What is claimed is:

1. A catheter for introducing and removing fluid to and from the vascular system comprising:

an elongated catheter body having a sidewall defining a catheter lumen, at least one opening in said catheter body at a first distal location of said catheter body, said at least one opening being adapted for relatively low pressure movement of fluid therethrough, a plurality of normally closed pressure responsive exits in said side wall, said plurality of exits positioned at a second location of said catheter body which is spaced from and proximal of said first distal location, said pressure responsive exits permitting fluid material to exit from said catheter lumen in response to an internal fluid pressure greater than a predetermined magnitude, an intermediate zone between said first distal location and said second location, a removable sealing member adapted to be positioned within said lumen, said sealing member having a sealing element, said sealing element being movable between a collapsed insertion state and an expanded sealing state, means for moving said sealing element between said collapsed insertion state and said expanded sealing state, whereby when said sealing member is positioned within said lumen and said sealing element is in said expanded sealing state at said intermediate zone, said sealing element will be expanded to contact the inside surface of said side wall of said lumen at said intermediate zone and thereby prevent flow of fluid between said first distal location and said second location so that fluid inserted through said lumen at a pressure greater than said predetermined magnitude will pass through said pressure responsive exits to contact and remove fibrin on the exterior surface of said elongated catheter body.

2. The catheter according to claim 1, wherein said sealing member comprises:

an elongated hollow shaft having an outside diameter less than the smallest inside dimension of said lumen so that said shaft is movable through said lumen, and said shaft having a distal and proximal end, said sealing element being carried by said shaft at said shaft distal end.

3. The catheter according to claim 2 wherein said sealing element comprises an expandable balloon connected to said shaft so that when said balloon is collapsed said sealing member is insertable into and removable from said lumen, and a hole in said shaft communicating with the interior of said balloon so that fluid inserted into the proximal end of said shaft will enter said balloon causing it to expand from its collapsed insertion state to its expanded sealing state to thereby engage the walls of said lumen.

4. The catheter according to claim 3 wherein said balloon is connected to said shaft at its distal end, said hole in said shaft located at the distal end of said shaft.

5. The catheter according to claim 3 wherein said shaft passes through said balloon so that said balloon surrounds said shaft, said hole in said shaft being at a location between the points where said shaft passes through said balloon so that fluid inserted into the proximal end of said shaft will exit said hole in said shaft into the interior of said balloon causing said balloon to expand from its collapsed state into its expanded sealing state.

6. The catheter according to claim 5 further comprising means for securing said balloon to said shaft at the points where said shaft passes therethrough.

7. The catheter according to claim 6 wherein said means for securing said balloon to said shaft is an adhesive.

8. The catheter according to claim 7 wherein said means for securing said balloon to said shaft is thermal bonded weld.

9. The catheter according to claim 6 wherein said balloon has a wall thickness of between 0.0005 inches and 0.020 inches.

10. The catheter according to claim 3 further comprising an adapter carried at the proximal end of said shaft for receiving fluid to be injected into said balloon.

11. The catheter according to claim 6 wherein said at least one opening in said catheter body at said first distal location is at the distal end of said catheter body.

12. The catheter according to claim 6 wherein there are a plurality of side wall openings at said first distal location.

13. The catheter according to claim 12 further comprising an end hole at the distal end of said catheter body, and a third distal zone distal of said first distal location, said sealing member when in said sealing state at said third distal zone being expanded to contact the inside surface of said lumen at said third distal zone to seal off said end hole and said first distal location from each other, said fluid inserted into said lumen being fibrin treating fluid, whereby, when said sealing element is in said sealing state at said third distal zone, fibrin treating fluid inserted through said lumen will flow through said side wall openings to clear said side wall openings of fibrin.

14. The catheter according to claim 12 wherein the distance between the points where said balloon is secured to said shaft is less than the distance between said first distal location and said second location.

15. The catheter according to claim 12 wherein the distance between the points where said balloon is secured to said shaft is larger than the longitudinal length of said first distal location so that when said sealing member is positioned within said lumen and said balloon is located at said first distal location said balloon will engage said sidewall openings when it is expanded into its expanded sealing state to seal off said plurality of openings.

16. The catheter according to claim 2 further comprising means carried by said shaft for locating the position of said shaft within said lumen.

17. The catheter according to claim 16 wherein said position locating means comprises a narrow band of radio opaque material for observation by fluoroscopy.

18. The catheter according to claim 17 wherein said band of radio opaque material is carried on said shaft between the points where said balloon is secured to said shaft.

19. The catheter according to claim 18 further comprising a narrow band of radio opaque material carried by said catheter body at said intermediate zone so that said band of radio opaque material on said shaft can be aligned with said band of radio opaque material on said catheter body in order to locate the position of said balloon in said intermediate zone.

20. The catheter according to claim 6 wherein a segment of said shaft between said points where said balloon is secured to said shaft has a diameter less than the diameter of said shaft on both the proximal and distal sides of said balloon, so that when said balloon is in its collapsed state the diameter of said shaft and balloon is substantially the same as the diameter of said shaft on the sides of said balloon.

21. The catheter according to claim 20 wherein said shaft on both the proximal and distal sides of said balloon is a size 4 French and the size of said shaft between said points where second shaft is secured to said balloon is a 3 French.

22. The catheter according to claim 21 wherein said balloon is a flexible polymer material.

23. The catheter according to claim 2 wherein the distance between said first distal location and said second location is between 0.15 inches and 0.25 inches.

24. The catheter according to claim 12 wherein there are six of said sidewall openings.

25. The catheter according to claim 2 wherein said sealing element comprises a covered wire mesh basket secured to the distal end of said shaft.

26. The catheter according to claim 25 wherein said covering on said wire mesh basket is flexible and impervious to fluid flow.

27. The catheter according to claim 26 wherein said means for moving said sealing element between said collapsed insertion state and said expanded sealing state comprises a wire extending through said shaft and longitudinally movable therethrough, and extending through said basket being connected at the distal end of said basket, and a handle carried at the proximal end of said wire and located beyond the proximal end of said shaft, whereby when said wire is moved in the proximal direction said distal end of said shaft causing said basket to expand in a radial direction into said expanded sealing state.

28. The catheter according to claim 2 wherein said catheter body is made of flexible material whereby when said fluid is inserted through said lumen at a pressure greater than said predetermined magnitude said catheter body will radially expand causing said fibrin to mechanically break apart.

29. A method for removing fibrin build up on the outside surface of a catheter having an elongated catheter body with a side wall defining a catheter lumen, at least one opening in said catheter body at a first distal location of said body and adapted for relatively low pressure movement of fluid therethrough, a plurality of normally closed pressure responsive exits in said side wall, said plurality of exits positioned at a second location of said catheter body which is spaced from and proximal of said first distal location, said pressure responsive exits permitting fluid material to exit from said catheter lumen in response to an internal fluid pressure greater than a predetermined magnitude, said method comprises:

injecting a fluid material into said lumen at a pressure greater than said predetermined magnitude so that said fluid material will pass through said pressure responsive exit slits to contact and remove fibrin from the exterior surface of said catheter body.

30. The method according to claim 29 further comprising the steps of:

inserting a sealing member having a sealing element movable between a collapsed state and an expanded state into said lumen prior to injecting said fluid material into said lumen, positioning said sealing element at a location within said lumen between said first distal location and said second location, and expanding said sealing element to its sealing state until it engages the inside surface of said side wall thereby preventing flow of fluid between said first distal location and said second location.

31. The method according to claim 30 wherein the step of positioning said sealing element within said lumen includes fluoroscopically observing a radio opaque marker carried by said sealing member as it is inserted in said lumen.

32. The method according to claim 31 wherein said radio opaque marker is a band of platinum iridium.

33. The method according to claim 29 wherein said fluid material is urokinase.

34. The method according to claim 29 wherein said fluid material is enzymatic fluid.

35. The method according to claim 29 wherein said fluid material is a non-reactive fluid.

* * * * *